(12) United States Patent
Reicher et al.

(10) Patent No.: US 8,094,901 B1
(45) Date of Patent: Jan. 10, 2012

(54) SYSTEMS AND METHODS FOR MATCHING, NAMING, AND DISPLAYING MEDICAL IMAGES

(75) Inventors: Murray A. Reicher, Rancho Santa Fe, CA (US); Evan K. Fram, Paradise Valley, AZ (US); Steven M. Greim, Oceanside, CA (US); John J. Schumacher, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 0 days.

(21) Appl. No.: 12/870,645

(22) Filed: Aug. 27, 2010

Related U.S. Application Data

(63) Continuation of application No. 11/265,978, filed on Nov. 3, 2005, now Pat. No. 7,787,672.

(60) Provisional application No. 60/625,690, filed on Nov. 4, 2004.

(51) Int. Cl.
*G06K 9/00* (2006.01)
*G06F 13/12* (2006.01)

(52) U.S. Cl. ............................ 382/128; 710/65; 600/407

(58) Field of Classification Search .......... 382/128–132; 710/65; 600/407
See application file for complete search history.

(56) References Cited

U.S. PATENT DOCUMENTS

| | | | |
|---|---|---|---|
| 4,672,683 A | 6/1987 | Matsueda | |
| 5,123,056 A | 6/1992 | Wilson | |
| 5,431,161 A | 7/1995 | Ryals et al. | |
| 5,452,416 A * | 9/1995 | Hilton et al. ................. | 715/783 |
| 5,542,003 A | 7/1996 | Wofford | |
| 5,734,915 A * | 3/1998 | Roewer ......................... | 715/202 |
| 5,740,267 A | 4/1998 | Echerer et al. | |
| 5,779,634 A | 7/1998 | Ema et al. | |
| 5,852,646 A | 12/1998 | Klotz et al. | |
| 5,926,568 A | 7/1999 | Chaney et al. | |
| 5,954,650 A * | 9/1999 | Saito et al. ..................... | 600/425 |
| 5,976,088 A | 11/1999 | Urbano et al. | |
| 5,987,345 A * | 11/1999 | Engelmann et al. .......... | 600/407 |
| 5,995,644 A | 11/1999 | Lai et al. | |
| 6,115,486 A | 9/2000 | Cantoni | |
| 6,151,581 A | 11/2000 | Kraftson et al. | |
| 6,175,643 B1 | 1/2001 | Lai et al. | |
| 6,185,320 B1 | 2/2001 | Bick et al. | |
| 6,304,667 B1 | 10/2001 | Reitano | |
| 6,347,329 B1 | 2/2002 | Evans | |
| 6,351,547 B1 | 2/2002 | Johnson et al. | |
| 6,424,996 B1 | 7/2002 | Killcommons et al. | |
| 6,463,169 B1 | 10/2002 | Ino et al. | |
| 6,532,299 B1 | 3/2003 | Sachdeva et al. | |
| 6,532,311 B1 | 3/2003 | Pritt | |
| 6,556,695 B1 | 4/2003 | Packer et al. | |
| 6,563,950 B1 | 5/2003 | Wiskott et al. | |

(Continued)

OTHER PUBLICATIONS

Interview Summary dated Dec. 1, 2010, in U.S. Appl. No. 12/702,976.

(Continued)

*Primary Examiner* — Manav Seth

(74) *Attorney, Agent, or Firm* — Knobbe Martens Olson & Bear LLP

(57) ABSTRACT

A method of matching medical images according to user-defined matches rules. In one embodiment, the matched medical images are displayed according user-defined display rules such that the matched medical images may be visually compared in manner that is suitable to the viewer's viewing preferences.

18 Claims, 2 Drawing Sheets

U.S. PATENT DOCUMENTS

| | | |
|---|---|---|
| 6,574,629 B1 | 6/2003 | Cooke et al. |
| 6,577,753 B2 * | 6/2003 | Ogawa ................. 382/132 |
| 6,603,494 B1 | 8/2003 | Banks et al. |
| 6,630,937 B2 | 10/2003 | Kallergi et al. |
| 6,678,764 B2 | 1/2004 | Parvelescu et al. |
| 6,697,506 B1 | 2/2004 | Oian et al. |
| 6,775,402 B2 | 8/2004 | Bacus et al. |
| 6,778,689 B1 | 8/2004 | Aksit et al. |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,917,696 B2 | 7/2005 | Soenksen |
| 6,996,205 B2 | 2/2006 | Capolunghi et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 * | 5/2006 | Mojsilovic et al. ............ 1/1 |
| 7,050,620 B2 | 5/2006 | Heckman |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,149,334 B2 | 12/2006 | Dehmeshki |
| 7,155,043 B2 | 12/2006 | Daw |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 * | 5/2007 | Belykh et al. ............ 382/128 |
| 7,224,852 B2 | 5/2007 | Lipton et al. |
| 7,260,249 B2 | 8/2007 | Smith |
| 7,263,710 B1 | 8/2007 | Hummel et al. |
| 7,272,610 B2 | 9/2007 | Torres |
| 7,412,111 B2 | 8/2008 | Battle et al. |
| 7,450,747 B2 | 11/2008 | Jabri et al. |
| 7,526,114 B2 | 4/2009 | Seul et al. |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,660,488 B2 | 2/2010 | Reicher et al. |
| 7,787,672 B2 | 8/2010 | Reicher et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 2002/0016718 A1 | 2/2002 | Rothschild et al. |
| 2002/0021828 A1 | 2/2002 | Papier et al. |
| 2002/0044696 A1 | 4/2002 | Sirohey et al. |
| 2002/0081039 A1 | 6/2002 | Funahashi |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0106119 A1 | 8/2002 | Foran et al. |
| 2002/0110285 A1 | 8/2002 | Wang et al. |
| 2002/0164063 A1 | 11/2002 | Heckman |
| 2002/0188637 A1 | 12/2002 | Bailey et al. |
| 2003/0028402 A1 | 2/2003 | Ulrich et al. |
| 2003/0036087 A1 | 2/2003 | Kaushikkar et al. |
| 2003/0053668 A1 | 3/2003 | Ditt et al. |
| 2003/0065613 A1 | 4/2003 | Smith |
| 2003/0115083 A1 | 6/2003 | Masarie et al. |
| 2003/0123717 A1 | 7/2003 | Bacus et al. |
| 2003/0185446 A1 | 10/2003 | Huang et al. |
| 2003/0195416 A1 | 10/2003 | Toth |
| 2004/0008900 A1 | 1/2004 | Jabri et al. |
| 2004/0024303 A1 | 2/2004 | Banks et al. |
| 2004/0068170 A1 | 4/2004 | Wang et al. |
| 2004/0086163 A1 | 5/2004 | Moriyama et al. |
| 2004/0088192 A1 | 5/2004 | Schmidt et al. |
| 2004/0101191 A1 | 5/2004 | Seul et al. |
| 2004/0114714 A1 | 6/2004 | Minyard et al. |
| 2004/0141661 A1 | 7/2004 | Hanna et al. |
| 2004/0151374 A1 | 8/2004 | Lipton et al. |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0170312 A1 | 9/2004 | Soenksen |
| 2004/0197015 A1 | 10/2004 | Fan et al. |
| 2004/0243435 A1 | 12/2004 | Williams |
| 2004/0254816 A1 | 12/2004 | Myers |
| 2004/0264753 A1 | 12/2004 | Capolunghi et al. |
| 2005/0027570 A1 | 2/2005 | Maier et al. |
| 2005/0036668 A1 | 2/2005 | McLennan et al. |
| 2005/0043970 A1 | 2/2005 | Hsieh |
| 2005/0063612 A1 | 3/2005 | Manber et al. |
| 2005/0065424 A1 * | 3/2005 | Shah et al. ............... 600/407 |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0184988 A1 | 8/2005 | Yanof et al. |
| 2005/0197860 A1 | 9/2005 | Joffe et al. |
| 2005/0273009 A1 | 12/2005 | Deischinger et al. |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111941 A1 | 5/2006 | Blom |
| 2006/0181548 A1 | 8/2006 | Hafey |
| 2006/0239573 A1 | 10/2006 | Novatzky et al. |
| 2007/0050701 A1 | 3/2007 | El Emam et al. |
| 2007/0055550 A1 | 3/2007 | Courtney et al. |
| 2007/0067124 A1 | 3/2007 | Kimpe et al. |
| 2007/0073556 A1 | 3/2007 | Lau et al. |
| 2007/0174079 A1 | 7/2007 | Kraus |
| 2007/0239481 A1 | 10/2007 | DiSilvestro et al. |
| 2008/0103828 A1 | 5/2008 | Squilla et al. |
| 2010/0138239 A1 | 6/2010 | Reicher et al. |
| 2010/0198608 A1 | 8/2010 | Kaboff et al. |
| 2010/0201714 A1 | 8/2010 | Reicher |
| 2011/0016430 A1 | 1/2011 | Fram |
| 2011/0267339 A1 | 11/2011 | Fram |

OTHER PUBLICATIONS

Notice of Allowance dated Oct. 8, 2010, in U.S. Appl. No. 11/268,261.

Notice of Allowance dated Dec. 3, 2010, in U.S. Appl. No. 11/268,261.

Notice of Allowance dated Jan. 6, 2011, in U.S. Appl. No. 11/268,261.

Interview Summary dated Nov. 16, 2010 in U.S. Appl. No. 11/265,979.

Final Office Action dated Dec. 23, 2010 in U.S. Appl. No. 11/265,979.

Final Office Action dated Oct. 28, 2010 in U.S. Appl. No. 11/268,262.

Interview Summary dated Dec. 1, 2010 in U.S. Appl. No. 11/268,262.

Notice of Allowance dated Dec. 1, 2010 in U.S. Appl. No. 11/268,262.

Final Office Action dated Nov. 26, 2010 in U.S. Appl. No. 11/942,673.

Interview Summary dated Dec. 3, 2010 in U.S. Appl. No. 11/942,687.

Final Office Action dated Dec. 23, 2010 in U.S. Appl. No. 11/944,027.

Non-Final Office Action dated Sep. 29, 2010 in U.S. Appl. No. 11/944,000.

Crowley, Rebecca et al., *Development of Visual Diagnostic Expertise in Pathology: an Information-processing Study*, Jan. 2003, Journal of the American medical Informatics Association, vol. 10, No. 1, pp. 39-51.

Non-Final Office Action dated Aug. 28, 2007 in U.S. Appl. No. 11/179,384.

Jan. 17, 2008 Response to Non-Final Office Action dated Aug. 28, 2007 in U.S. Appl. No. 11/179,384.

Final Office Action dated Jun. 26, 2008 in U.S. Appl. No. 11/179,384.

Non-Final Office Action dated Dec. 29, 2008 in U.S. Appl. No. 11/179,384.

Final Office Action dated Jul. 24, 2009, in U.S. Appl. No. 11/179,384.

Notice of Allowance dated Nov. 3, 2009, in U.S. Appl. No. 11/179,384.
Non-Final Office Action dated Aug. 18, 2010 in U.S. Appl. No. 12/702,976.
Non-Final Office Action dated Oct. 1, 2009, in U.S. Appl. No. 11/268,261.
Notice of Allowance dated Feb. 2, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Interview Summary dated May 14, 2010, in U.S. Appl. No. 11/268,261.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 26, 2010 in U.S. Appl. No. 11/942,673.
Interview Summary dated Jul. 26, 2010 in U.S. Appl. No. 11/942,673.
NonFinal Office Action dated Sep. 16, 2010 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated May 16, 2011, in U.S. Appl. No. 12/857,915.
Interview Summary dated Mar. 17, 2011 in U.S. Appl. No. 11/265,979.
Notice of Allowance dated May 26, 2011 in U.S. Appl. No. 11/265,979.
Notice of Allowance dated Feb. 25, 2011 in U.S. Appl. No. 11/268,262.
Non-Final Office Action dated May 5, 2011 in U.S. Appl. No. 12/870,645.
Interview Summary dated Mar. 2, 2011 in U.S. Appl. No. 11/942,674.
Notice of Allowance, dated Apr. 1, 2011 in U.S. Appl. No. 11/942,674.
Final Office Action, dated Apr. 5, 2011 in U.S. Appl. No. 11/942,687.
Interview Summary dated Mar. 31, 2011 in U.S. Appl. No. 11/944,027.
Final Office Action dated Apr. 20, 2011 in U.S. Appl. No. 11/944,000.
Interview Summary dated Jun. 7, 2011 in U.S. Appl. No. 11/944,000.
Interview Summary dated Sep. 6, 2011, in U.S. Appl. No. 12/857,915.
Non Final Office Action Dated Nov. 10, 2011 in U.S. Appl. No. 13/118,085.
Non Final Office Action Dated Dec. 1, 2011 in U.S. Appl. No. 13/228,349.
US 7,801,341, 09/2010, Fram et al. (withdrawn)

\* cited by examiner

SYSTEMS AND METHODS FOR MATCHING, NAMING, AND DISPLAYING MEDICAL IMAGES

CROSS-REFERENCE TO RELATED APPLICATIONS

This application is a continuation of U.S. application Ser. No. 11/265,978, filed Nov. 3, 2005, entitled "SYSTEMS AND METHODS FOR MATCHING, NAMING, AND DISPLAYING MEDICAL IMAGES," which claims priority under 35 U.S.C. §119(e) to U.S. Provisional Application Ser. No. 60/625,690, filed on Nov. 4, 2004, each of which are hereby expressly incorporated by reference in their entirety.

BACKGROUND OF THE INVENTION

1. Field of the Invention

This invention relates to matching, naming, and displaying medical images based upon user-defined rules.

2. Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. When medical images are created, they are typically provided an identifier, label, or name. This name can be either automatically generated or provided by a technician. One problem with organizing medical images from different sources is that these identifiers do not necessarily provide a good description that is understandable to a subsequent viewer of the image. Furthermore, as the number of images increase, there is a need for improved methods of matching related medical images together for subsequent viewing and analysis.

SUMMARY OF THE INVENTION

One embodiment comprises a method of displaying medical data. The method comprises receiving a plurality of medical images of a first medical examination and receiving at least one user-defined matching rules, at least one of user-defined matching rules identifying selection criteria for the medical images. The method also comprises selecting medical images that satisfy the selection criteria of the user-defined rules, thereby matching medical images according to user-specific rules and receiving at least one user-defined display rule, at least one of user-defined display rules identifying a display preference with respect to selected medical images. The method also comprises displaying the selected medical images according to the identified display preferences, thereby allowing matched medical images to be visually compared and displayed in a manner that is suitable to the user's preferences.

Another embodiment comprises a method displaying medical data. The method comprises receiving a plurality of medical images of a first medical examination and receiving a plurality of medical images of a second medical examination. The method also comprises receiving at least one user-defined matching rule, at least one of user-defined matching rules identifying selection criteria for matching the medical images of the first and second medical examinations. The method also comprises selecting medical images that satisfy the selection criteria of the user-defined rules, thereby matching medical images of the first medical examination with medical images of the second examination according to user-specific rules. The method also comprises receiving a plurality of user-defined display rules, at least one of user-defined display rules identifying a display preference with respect to selected medical images. The method also comprises displaying the selected medical images according to the identified display preferences, thereby allowing matched medical images to be visually compared and displayed in a manner that is suitable to the user's preferences.

Another embodiment comprises a system for displaying medical data. The system comprises an electronic device being configured to receive a plurality of medical images of a first medical examination. The electronic device is configured to receive a plurality of user-defined matching rules. At least one of user-defined matching rules identify selection criteria for the medical images. The electronic device is further configured to select medical images that satisfy the selection criteria of the user-defined rules, thereby matching medical images according to user-specific rules. The electronic device is further configured to receive a at least one user-defined display rules. At least one of user-defined display rules identify a display preference with respect to selected medical images. The electronic device is further being configured to display the selected medical images according to the identified display preferences, thereby allowing matched medical images to be visually compared and displayed in a manner that is suitable to the user's preferences.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
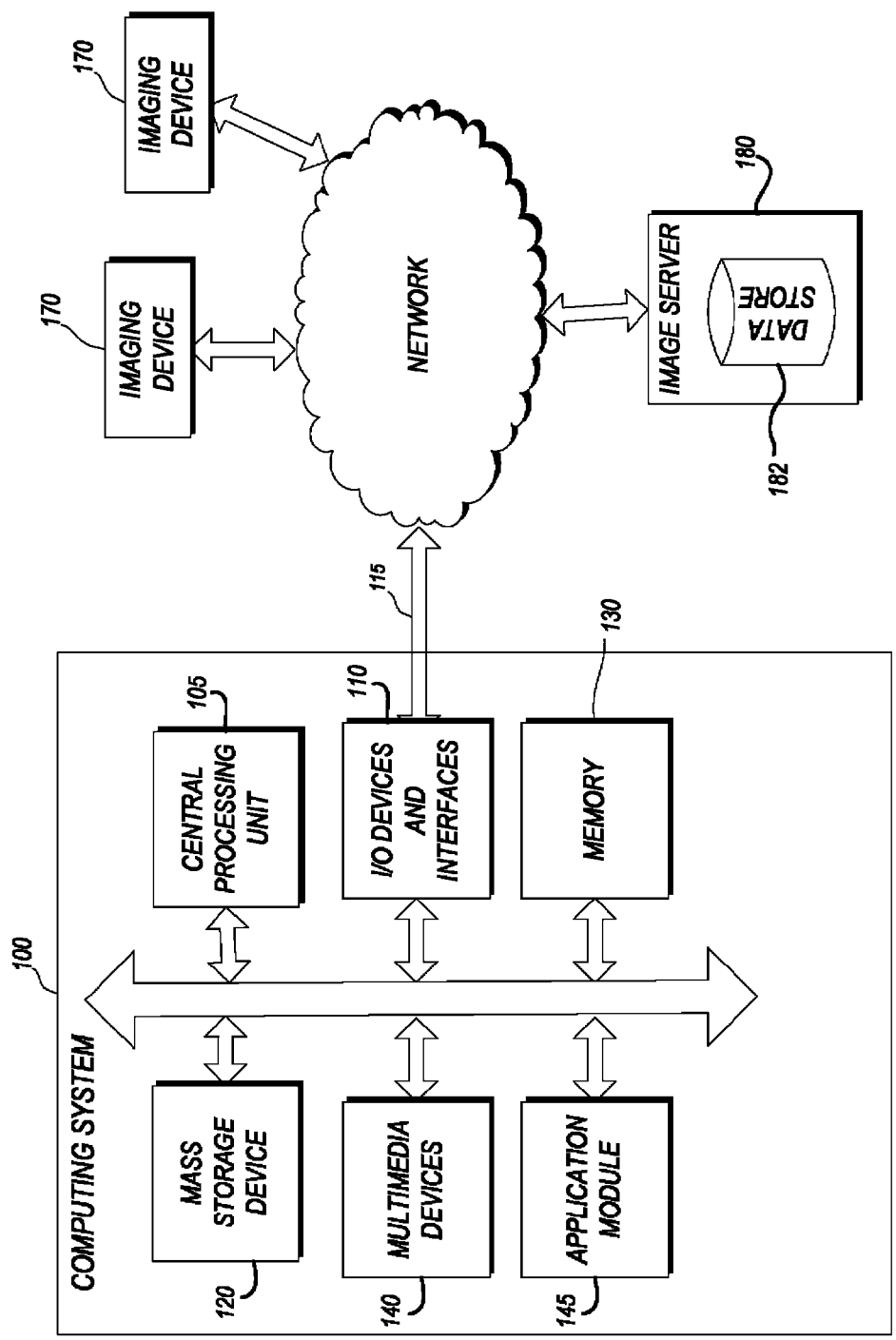
FIG. 1 is a block diagram of an exemplary computing system in communication with a network and various networked devices.

FIG. 1 is a block diagram of an exemplary computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

The computing system 100 includes, for example, a personal computer that is IBM, Macintosh, or Linux/Unix compatible. In one embodiment, the exemplary computing system 100 includes a central processing unit ("CPU") 105, which may include a conventional microprocessor, an application module 145 that comprises one or more various applications that may be executed by the CPU 105. The application module 145 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server 180 via the network 160 and image information is transmitted to the image server 180 and stored in the data store 182.

In one embodiment, the image data is stored in Digital Imaging and Communications in Medicine ("DICOM") format. The complete DICOM specifications may be found on the National Electrical Manufactures Association Website at <medical.nema.org>. Also, NEMA PS 3—Digital Imaging and Communications in Medicine, 2004 ed., Global Engineering Documents, Englewood Colo., 2004, provides an overview of the DICOM standard. Each of the above-cited references is hereby incorporated by reference in their entireties. In one embodiment, the data store 182 also stores the user-defined display rules associated with one or more of the images stored on the data store 182. As discussed in further detail below, the user-defined display rules may vary depending of the type of image, area imaged, clinical indication, source of image, display device, user, or other factors. Accordingly, any type of user-defined display rule is expressly contemplated for use in conjunction with the systems and methods described herein.

The exemplary image server 160 is configured to store images from multiple sources and in multiple formats. For example, the image server 160 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

DEFINITION OF TERMS

Below is a definition of certain terms used herein.

"Modality" is defined as a medical imaging device (a patient who undergoes an MRI is said to have been examined or scanned with the MRI modality).

"Medical image" is defined to include an image of an organism. It may include but is not limited to a radiograph, computed tomography (CT), magnetic resonance imaging (MRI), Ultrasound (US), mammogram, positron emission tomography scan (PET), nuclear scan (NM), pathology, endoscopy, ophthalmology, or many other types of medical images. While this description is directed to viewing and tracking of medical images, the methods and systems described herein may also be used in conjunction with non-medical images, such as, images of circuit boards, airplane wings, and satellite images, for example.

"Patient" refers to an individual who undergoes a medical imaging examination.

"Viewing" is defined to include the process of visually observing one or more medical images associated with exams.

"Viewer" is defined as any person who views a medical image.

"Reading" is defined to include the process of visually observing one or more medical images for the purpose of creating a professional medical report, also called an interpretation. When reading is complete, an exam may be labeled "read," indicating that the medical professional has completed observation of the one or more medical images for purposes of creating a medical report.

"Reader" is defined to include one who is authorized to perform the reading process.

"User" is defined to include any person that is a viewer and/or a reader.

"Display rules" are defined to include methods of display of an image or exam. For example, an image or exam may be displayed with a certain pixel window level or width (similar to brightness and contrast), in color, based on a certain color map, opacity map, or other display parameters.

"User-defined display rules" refers to rules that a user can establish and store in a database that establish criteria for image display that is considered adequate. For example, a user-defined display rule might store a rule that triggers certain warnings or displays if all pixels in a medical image have not been displayed or, alternatively, if at least a predetermined portion of the pixels have not been displayed with a certain display method (such as image window, level, brightness, contrast, opacity, color look-up table, or other parameters). User-defined display rules may also refer to other image processing functions, such as edge enhancement and automated image analysis functions, e.g., computer-aided detection (CAD) techniques.

Figure 2:
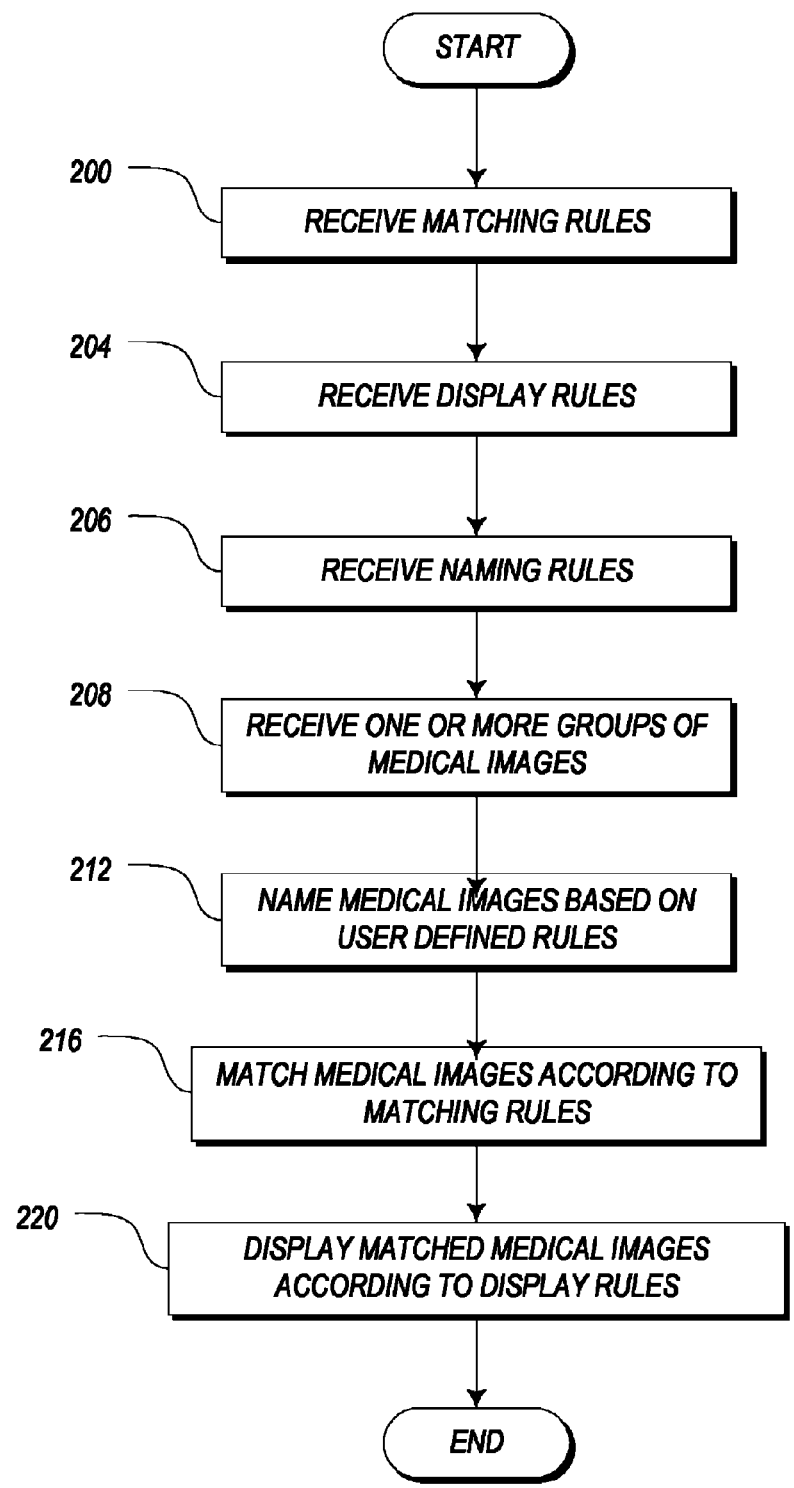
FIG. 2 is a flowchart illustrating an exemplary process of matching and displaying medical images.

FIG. 2 is a high-level flowchart describing an exemplary method that may be performed by the computing system 100 (FIG. 1). Depending on the embodiment, additional steps may be added, others removed, and the ordering of the steps rearranged.

Starting at step 200, matching rules are provided with respect to medical images that are accessible by the computer system 100. The medical can be accessible via the imaging server 180, be local to the computing system 100, or elsewhere accessible via the network 160. The matching rules establish criteria for matching related medical images. In one embodiment, the matching rules are defined for a particular individual or machine. In another embodiment, the matching rules are defined for a group or class of individuals. The rules may be provided by the users themselves and/or by a system administrator. The auto-matching rules may be established to select medical data based upon any of the following non-limiting criteria: modality (MRI, CT, X-ray etc); exam type (left knee X-ray, CT Chest, MRI Brain etc); archive status (has the exam been archived, archived and restored, not yet archived); assigned physician (has the exam been assigned to a particular physician for interpretation); exam age (how long ago was the exam done); patient age; and any item in a DICOM header file, such as orientation, contrast use, thickness of slices, field of view, MRI tissue contrast weighting, and other items. With regard to some criteria, such as MRI tissue contrast weighting, the rules may analyze the MRI pulse sequence and the imaging parameters in order to determine the tissue contrast weighting and subcategorize images into weighting categories or weighting names.

The matching rules can be used to match medical images in the same and/or different medical series. For example, assume the medical images relate to three series of 6 x-rays. The matching rules can be established such that like views amongst each of the different series are grouped together for subsequent viewing. The matching rules be defined using simple or complex search expressions such "AND" or "OR." Complex filter criteria may be stored on the image server 180 and then used by local devices that access these records via the web.

Next, at a step 204, display rules are provided with respect to the medical images. In one embodiment, the display rules may be user-defined allowing the user to determine the timing, positioning, and size of displayed matched images. For example, a user can define that matched medical images are all displayed concurrently on a display. Also, for example, a user can define that the most recent of the matched medical images are displayed on the left hand portion of the display and the other matched medical images are displayed in sequence on the right hand side of the display, the sequence advancing in response to user prompting. In one embodiment, the display rules include directives (timing, positioning, and size). As an example, directives can include the following for identifying location information: TOP_DISPLAY, BOTTOM_DISPLAY, RIGHT_DISPLAY, LEFT_DISPLAY, CENTER DISPLAY. Furthermore, if the number of matched medical images is variable, the display rules can include instructions for identifying selected medical images based upon further rules, such as using the matching criteria listed above. In addition, the display rules may or may not define how many images or image series are displayed per monitor, a display grid (2×3, 5×4, etc.), or whether like images are displayed neighboring each other side by side horizontally or vertically. Furthermore, the display rules may also specify how different matched medical images from different series may be "interleaved" together for successive display. Using the computing system 100, a user may also manually interleave matched medical images, e.g., order the matched medical images for progressive display of each of the matched sets. The computing system 100 may also provide an interface to re-order images or image series to facilitate the matching display, and may even reorient images (flip, rotate) in order to best match the display. Using the display rules, the user can provide display rules such that related medical images are readily comparable.

In one embodiment, display rules may be set to display pre and post contrast axial T1 weighted images from a brain MRI from the same exam in adjacent panes on a monitor. Display rules may also be set to display axial T2 weighted MRI images from a prior spine MRI adjacent to axial T2 weighted images from the current exam. Display rules may also be set to display a PA projection from a chest radiograph from a prior exam adjacent to the same projection from the current exam.

Continuing to a step 206, naming rules are provided. The naming rules describe how the medical images can be provided a new "name", label, or identifying description. In one embodiment, the naming rules are defined for a particular individual or machine. In another embodiment, the matching rules are defined for a group or class of individuals. The rules may be provided by the users themselves and/or by a system administrator. The naming rules can define sets of naming rules for different exam types or other classifications. The naming rules can also be defined to perform naming before or after the matching step 216. In one embodiment, the naming rules define how information in a header file, e.g., DICOM file, that is associated with the medical image is described. The naming rules can define that the new name of the medical image is defined using meta or other data that is associated with the medical images. It is noted that the new name of the medical image need not be stored with the image but such information can be stored by any device connected to the network.

Continuing to a step 208, in one embodiment, the medical images are received by the computing system 100. It is noted that in one embodiment, the medical images need not be stored locally by the computer system 100 but are merely made accessible to it via the network Continuing to a step 212, the computing system 100 may optionally name the received medical images based upon the received user-specific naming rules. In one embodiment, the new "names" of the medical images may be used by the computing system 100 to facilitate matching (step 216) of related medical images. In one embodiment, the naming rules define how information in a header file, e.g., a DICOM file, is described. The naming rules can define that the "new" name of the medical image is defined using meta or other data that is associated with the medical image. For example, the naming rules can define that the new "name" of the medical image is based upon the name of patient, the exam type, and the date of the medical image. Also for example, the naming rules can define categorization tables that define a particular name when certain conditions are met. The particular name can be predefined and/or based upon meta or other data that is associated with the medical images.

Proceeding to a step 216, the computing system 100 matches medical images in the same or related series together as discussed above (step 200). The matched images may be collectively or individually provided a new name per the naming rules provided in step 206. Continuing to a step 220, the matched medical images are displayed. It is noted that the display rules may define user display preferences that are specific for particular types of medical images, e.g., the imaging modality, the body part, whether there is one exam, two, or more medical images being displayed. The display rules may be defined per individual user, site, or system. In one embodiment, the user can store the display rules in a database. In one embodiment, one set of display rules can apply to one modality and another set of display rules can apply to another modality. In addition, the display rules may include specific triggers or warnings that occur if the user-defined display rules are not satisfied.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of displaying medical data, the method comprising:
   receiving a plurality of medical images of a first medical examination;
   receiving at least one user-defined matching rule including at least one user-defined matching rule identifying selection criteria for selecting medical images;
   selecting medical images that satisfy the selection criteria of the user-defined matching rules, thereby matching medical images according to user-specific rules;
   receiving at least one user-defined display rule including at least one user-defined display rule identifying a display preference with respect to the selected medical images; and
   displaying the selected medical images according to the identified display preference, thereby allowing the matched medical images to be visually compared and displayed in a manner that is suitable to user preferences, wherein at least some of the steps are performed by a computer system having one or more processors.

2. The method of claim 1, additionally comprising naming the matched medical images according to at least one user-defined naming rule.

3. The method of claim 1, additionally comprising naming the medical images according to at least one user-defined naming rule prior to said selecting.

4. The method of claim 1, wherein the medical images are grouped in one or more image series.

5. The method of claim 1, additionally comprising:
   receiving a second plurality of medical images of a second medical examination; and
   selecting medical images of the first medical examination and the second medical examination that satisfy the selection criteria of the user-defined rules, thereby allowing a user to match medical images of the first medical examination with medical images of the second medical examination according to user-specific rules.

6. The method of claim 5, additionally comprising:
   receiving at least one second user-defined display rule, the second user-defined display rule identifying a display preference with respect to matched medical images of the first and second examinations; and
   displaying the matched medical images in accordance with the second user-defined display rules.

7. The method of claim 5, additionally comprising displaying the matched medical images in accordance with the user-defined display rules.

8. The method of claim 1, additionally comprising:
   receiving a plurality of second user-defined matching rules, at least one of the user-defined matching rules identifying second selection criteria for matching the selected medical images of the first examination with medical images of a second medical examination; and
   selecting medical images of the first medical examination and the second medical examination that satisfy the second selection criteria of the user-defined rules, thereby allowing a user to match medical images of the first medical examination with medical images of the second medical examination according to user-specific rules.

9. The method of claim 8, additionally comprising:
   receiving a plurality of second user-defined display rules, at least one of the second user-defined display rules identifying a display preference with respect to matched medical images of the first and second examinations; and
   displaying the matched medical images in accordance with the second user-defined display rules.

10. The method of claim 8, additionally comprising displaying the matched medical images in accordance with the user-defined display rules.

11. A system for displaying medical data, the system comprising:
    an electronic device configured to receive a plurality of medical images of a first medical examination, the electronic device being further configured to receive a plurality of user-defined matching rules, at least one of the user-defined matching rules identifying selection criteria, the electronic device being further configured to select medical images that satisfy the selection criteria of the user-defined matching rules, thereby matching medical images according to user-specific rules, the electronic device being further configured to receive a plurality of user-defined display rules, at least one of the user-defined display rules identifying a display preference with respect to selected medical images; and the electronic device being further configured to display the selected medical images according to the identified display preferences, thereby allowing matched medical images to be visually compared and displayed in a manner that is suitable to user preferences.

12. The system of claim 11, wherein the medical images are grouped in one or more image series.

13. The system of claim 11, wherein the electronic device is configured to receive a second plurality of medical images of a second medical examination and select medical images of the first medical examination and the second medical examination that satisfy the selection criteria of the user-defined rules, thereby allowing a user to match medical images of the first medical examination with medical images of the second medical examination according to user-specific rules.

14. The system of claim 13, wherein the electronic device is further configured to receive a plurality of second user-defined display rules, at least one of the second user-defined display rules identifying a display preference with respect to matched medical images of the first and second examinations; and wherein the electronic device is further configured to display the matched medical images in accordance with the second user-defined display rules.

15. The system of claim 14, wherein the electronic device is further configured to display the matched medical images in accordance with the user-defined display rules.

16. The system of claim 11, wherein the electronic device is configured to receive a plurality of second user-defined matching rules, at least one of the user-defined matching rules identifying second selection criteria for matching the selected medical images of the first examination with medical images of a second medical examination; and wherein the electronic device is configured to select medical images of the first medical examination and of second medical examination that satisfy the second selection criteria of the user-defined rules, thereby allowing a user to match medical images of the first medical examination with medical images of the second medical examination according to user-specific rules.

17. The system of claim 16, wherein the electronic device is configured to receive a plurality of second user-defined display rules, at least one of the second user-defined display rules identifying a display preference with respect to matched medical images of the first and second examinations, and wherein the electronic device is configured to display matched medical records in accordance with the second user-defined display rules.

18. The system of claim 16, wherein the electronic device is configured to display matched medical records in accordance with the user-defined display rules.

* * * * *